(12) United States Patent
Lin et al.

(10) Patent No.: US 8,993,350 B2
(45) Date of Patent: Mar. 31, 2015

(54) SENSITIVE METHOD TO ANALYSE FREE PEG-MALEIMIDE

(75) Inventors: Mei Lin, Plainsboro, NJ (US); Anulfo Valdez, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 29 days.

(21) Appl. No.: 13/146,335

(22) PCT Filed: Jan. 29, 2010

(86) PCT No.: PCT/US2010/022463
§ 371 (c)(1),
(2), (4) Date: Jul. 26, 2011

(87) PCT Pub. No.: WO2010/088436
PCT Pub. Date: Aug. 5, 2010

(65) Prior Publication Data
US 2012/0021533 A1    Jan. 26, 2012

Related U.S. Application Data

(60) Provisional application No. 61/148,530, filed on Jan. 30, 2009.

(51) Int. Cl.
*G01N 33/533* (2006.01)
*G01N 21/76* (2006.01)
*C07K 1/14* (2006.01)
*G01N 33/53* (2006.01)

(52) U.S. Cl.
CPC ........ *G01N 33/5308* (2013.01); *G01N 2440/28* (2013.01)
USPC ........... 436/546; 435/172; 530/344; 530/408; 530/412; 530/417

(58) Field of Classification Search
CPC ... G01N 33/582; G01N 33/533; Y10S 436/80
See application file for complete search history.

(56) References Cited

U.S. PATENT DOCUMENTS 6,828,401 B2    12/2004 Nho et al.

OTHER PUBLICATIONS

Singh, Rajeeva. A sensitive assay for maleimide groups. Bioconjugate Chem. 1994, vol. 5, pp. 348-351.*
Ananda, K. et al., "Analysis of functionalization of methoxy-PEG as maleimide-PEG", Analytical Biochemistry, vol. 374, pp. 231-242 (2008).
Delahunty, T. et al., "New Liquid-Chromatographic Method for Measuring Polyethylene Glycol in Urine", Clinical Chemistry, vol. 32, No. 2, pp. 351-353 (1986).
Oliva, A. et al., "HPLC Determination of Polyethylene Glycol 400 in Urine: Oligomeric Profile in Healthy and Celiac Disease Subjects", Clinical Chemistry, vol. 40, No. 8, pp. 1571-1574 (1994).

* cited by examiner

*Primary Examiner* — Shafiqul Haq
(74) *Attorney, Agent, or Firm* — Nickki L. Parlet

(57) ABSTRACT

The present invention relates generally to a novel method using HPLC and fluorescence detection of free PEG-mal in PEGylated proteins and PEG-mal raw materials by adding a fluorescent label to the free PEG-mal.

10 Claims, 15 Drawing Sheets

FIG 1
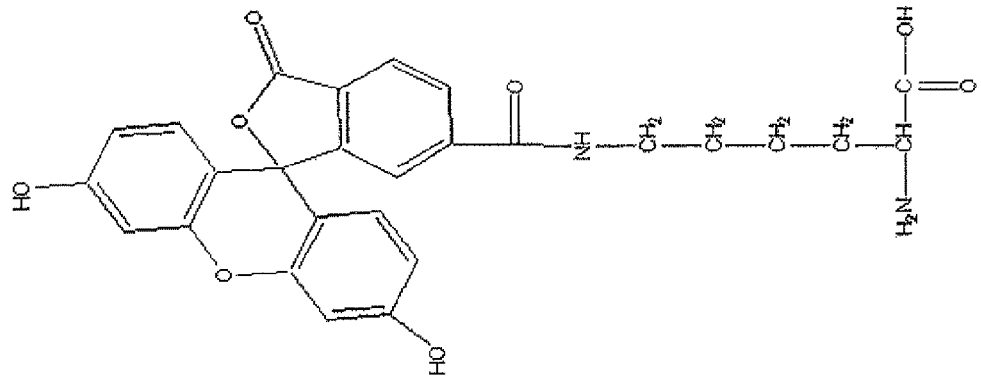
[Kfl]= Lysine with Fluorescein
Ten Amino Acids Peptide Probe (10AA):
CWTGSPHDT[Kfl]
Two Amino Acids Peptide Probe (2AA):
*C[Kfl]
* = Acetylated N-terminus & Amidated C-terminus
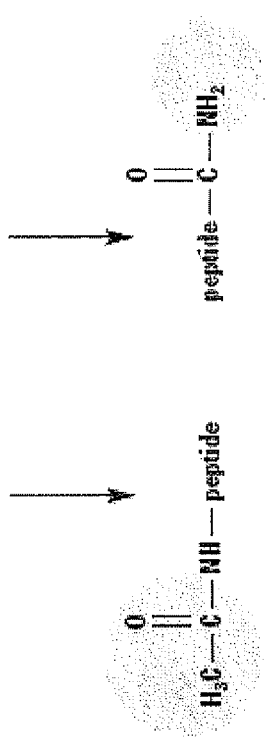

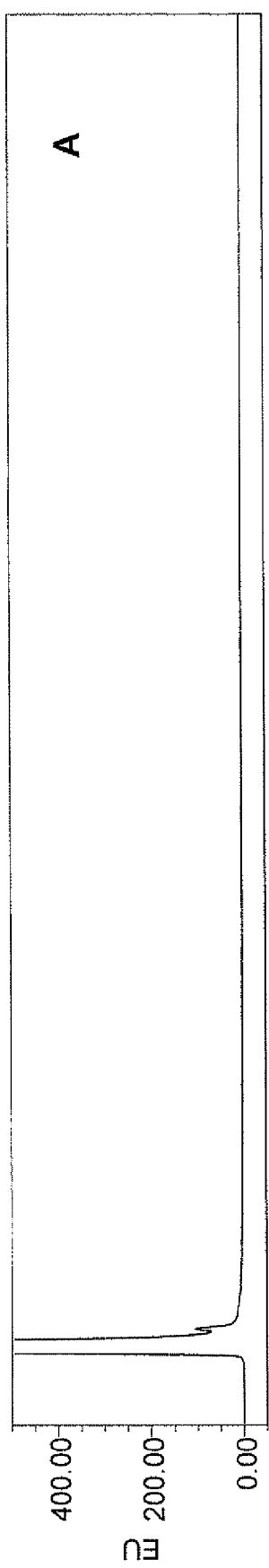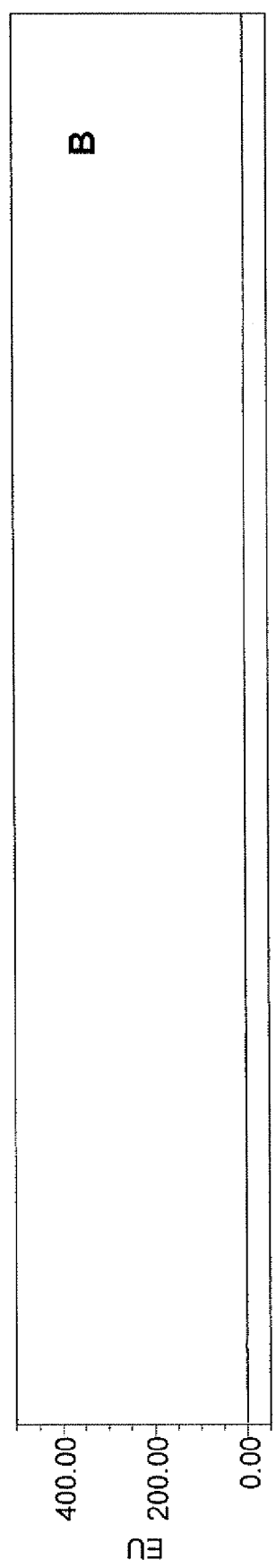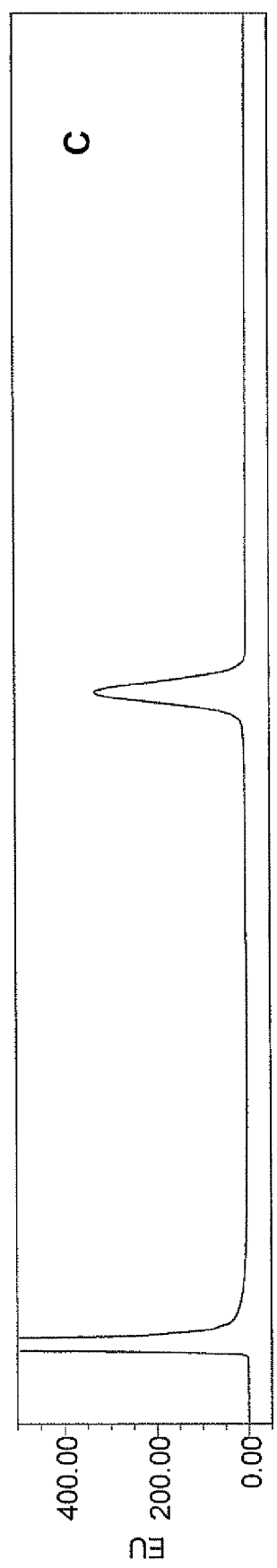
FIG. 5

System Suitability Separation Results

| | Name | RT | USP Resolution | USP Tailing | K Prime | Width @ Tangent | s/n |
|---|---|---|---|---|---|---|---|
| 1 | P40KB_Lab | 16.894 | | 0.989648 | 7.891622 | 0.819078 | 5.260988 | ary art. In general, PEG is used in its meth- was found

SEQUENCE LISTING

<160> NUMBER OF SEQ ID NOS: 8

<210> SEQ ID NO 1
<211> LENGTH: 20
<212> TYPE: PRT
<213> ORGANISM: Artificial Sequence
<220> FEATURE:
<223> OTHER INFORMATION: synthesized polypeptide
<220> FEATURE:
<221> NAME/KEY: MISC_FEATURE
<222> LOCATION: (2)..(19)
<223> OTHER INFORMATION: Xaa one or more of amino acids 2-19 may be
      present or absent: Xaa represents amino acid(s):
      Ala,Cys,Asp,Gln,Phe,Gly,His,Ile,Lys,Leu,Met,Asn,Pro,Gln,Arg,Ser,
      Thr,Val,Trp,Tyr
<220> FEATURE:
<221> NAME/KEY: MISC_FEATURE
<222> LOCATION: (20)..(20)
<223> OTHER INFORMATION: Lys is labeled with fluorophore

<400> SEQUENCE: 1

Cys Xaa Xaa Xaa Xaa Xaa Xaa Xaa Xaa Xaa Xaa Xaa Xaa Xaa Xaa
1               5                   10                  15

Xaa Xaa Xaa Lys
            20

<210> SEQ ID NO 2
<211> LENGTH: 20
<212> TYPE: PRT
<213> ORGANISM: Artificial Sequence
<220> FEATURE:
<223> OTHER INFORMATION: synthesized polypeptide
<220> FEATURE:
<221> NAME/KEY: MISC_FEATURE
<222> LOCATION: (1)..(1)
<223> OTHER INFORMATION: Lys is labeled with fluorophore
<220> FEATURE:
<221> NAME/KEY: MISC_FEATURE
<222> LOCATION: (2)..(19)
<223> OTHER INFORMATION: Xaa one or more of amino acids 2-19 may be
      present or absent: Xaa represents amino acid(s):
      Ala,Cys,Asp,Gln,Phe,Gly,His,Ile,Lys,Leu,Met,Asn,Pro,Gln,Arg,Ser,
      Thr,Val,Trp,Tyr

<400> SEQUENCE: 2

Lys Xaa Xaa Xaa Xaa Xaa Xaa Xaa Xaa Xaa Xaa Xaa Xaa Xaa Xaa
1               5                   10                  15

Xaa Xaa Xaa Cys
            20

<210> SEQ ID NO 3
<211> LENGTH: 20
<212> TYPE: PRT
<213> ORGANISM: Artificial Sequence
<220> FEATURE:
<223> OTHER INFORMATION: synthesized polypeptide
<220> FEATURE:
<221> NAME/KEY: MISC_FEATURE
<222> LOCATION: (1)..(1)
<223> OTHER INFORMATION: Cys is blocked
<220> FEATURE:
<221> NAME/KEY: MISC_FEATURE
<222> LOCATION: (2)..(19)
<223> OTHER INFORMATION: Xaa one or more of amino acids 2-19 may be
      present or absent: Xaa represents amino acid(s):
      Ala,Cys,Asp,Gln,Phe,Gly,His,Ile,Lys,Leu,Met,Asn,Pro,Gln,Arg,Ser,
      Thr,Val,Trp,Tyr
<220> FEATURE:
<221> NAME/KEY: MISC_FEATURE
<222> LOCATION: (20)..(20)
<223> OTHER INFORMATION: Lys is labeled with fluorophore

```
<400> SEQUENCE: 3

Cys Xaa Xaa Xaa Xaa Xaa Xaa Xaa Xaa Xaa Xaa Xaa Xaa Xaa Xaa
1               5                   10                  15

Xaa Xaa Xaa Lys
            20

<210> SEQ ID NO 4
<211> LENGTH: 20
<212> TYPE: PRT
<213> ORGANISM: Artificial Sequence
<220> FEATURE:
<223> OTHER INFORMATION: synthesized polypeptide
<220> FEATURE:
<221> NAME/KEY: MISC_FEATURE
<222> LOCATION: (2)..(19)
<223> OTHER INFORMATION: Xaa one or more of amino acids 2-19 may be
      present or absent: Xaa represents amino acid(s):
      Ala,Cys,Asp,Gln,Phe,Gly,His,Ile,Lys,Leu,Met,Asn,Pro,Gln,Arg,Ser,
      Thr,Val,Trp,Tyr
<220> FEATURE:
<221> NAME/KEY: MISC_FEATURE
<222> LOCATION: (20)..(20)
<223> OTHER INFORMATION: Lys is labeled with fluorophore
      Lys is blocked

<400> SEQUENCE: 4

Cys Xaa Xaa Xaa Xaa Xaa Xaa Xaa Xaa Xaa Xaa Xaa Xaa Xaa Xaa
1               5                   10                  15

Xaa Xaa Xaa Lys
            20

<210> SEQ ID NO 5
<211> LENGTH: 20
<212> TYPE: PRT
<213> ORGANISM: Artificial Sequence
<220> FEATURE:
<223> OTHER INFORMATION: synthesized polypeptide
<220> FEATURE:
<221> NAME/KEY: MISC_FEATURE
<222> LOCATION: (1)..(1)
<223> OTHER INFORMATION: Cys is blocked
<220> FEATURE:
<221> NAME/KEY: MISC_FEATURE
<222> LOCATION: (2)..(19)
<223> OTHER INFORMATION: Xaa one or more of amino acids 2-19 may be
      present or absent: Xaa represents amino acid(s):
      Ala,Cys,Asp,Gln,Phe,Gly,His,Ile,Lys,Leu,Met,Asn,Pro,Gln,Arg,Ser,
      Thr,Val,Trp,Tyr
<220> FEATURE:
<221> NAME/KEY: MISC_FEATURE
<222> LOCATION: (20)..(20)
<223> OTHER INFORMATION: Lys is labeled with fluorophore
      Lys is blocked

<400> SEQUENCE: 5

Cys Xaa Xaa Xaa Xaa Xaa Xaa Xaa Xaa Xaa Xaa Xaa Xaa Xaa Xaa
1               5                   10                  15

Xaa Xaa Xaa Lys
            20

<210> SEQ ID NO 6
<211> LENGTH: 36
<212> TYPE: PRT
<213> ORGANISM: Artificial
<220> FEATURE:
<223> OTHER INFORMATION: synthesized polypeptide
<220> FEATURE:
<221> NAME/KEY: MISC_FEATURE
<222> LOCATION: (1)..(1)
<223> OTHER INFORMATION: Xaa can be any naturally occurring amino acid
```

```
<220> FEATURE:
<221> NAME/KEY: MISC_FEATURE
<222> LOCATION: (1)..(17)
<223> OTHER INFORMATION: Xaa amino acids 1-17 plus 19-35 total no more
      than 18
<220> FEATURE:
<221> NAME/KEY: MISC_FEATURE
<222> LOCATION: (2)..(17)
<223> OTHER INFORMATION: Xaa one or more of amino acids 2-17 may be
      present or absent: Xaa represents amino acid(s):
      Ala,Cys,Asp,Gln,Phe,Gly,His,Ile,Lys,Leu,Met,Asn,Pro,Gln,Arg,Ser,
      Thr,Val,Trp,Tyr
<220> FEATURE:
<221> NAME/KEY: MISC_FEATURE
<222> LOCATION: (2)..(17)
<223> OTHER INFORMATION: Xaa one or more of amino acids 2-17 may be
      present or absent: Xaa represents amino acid(s):
      Ala,Cys,Asp,Gln,Phe,Gly,His,Ile,lys,Leu,Met,Asn,Pro,Gln,Arg,Ser,
      Thr,Val,Trp,Tyr
<220> FEATURE:
<221> NAME/KEY: MISC_FEATURE
<222> LOCATION: (18)..(18)
<223> OTHER INFORMATION: Lys is labeled with fluorophore
<220> FEATURE:
<221> NAME/KEY: MISC_FEATURE
<222> LOCATION: (19)..(35)
<223> OTHER INFORMATION: Xaa amino acids 19-35 plus 1-17 total no more
      than 18
<220> FEATURE:
<221> NAME/KEY: MISC_FEATURE
<222> LOCATION: (19)..(19)
<223> OTHER INFORMATION: Xaa can be any naturally occurring amino acid
<220> FEATURE:
<221> NAME/KEY: MISC_FEATURE
<222> LOCATION: (20)..(35)
<223> OTHER INFORMATION: Xaa one or more of amnio acids 20-35 may be
      present or absent Xaa represents amino acid(s):
      Ala,Cys,Asp,Gln,Phe,Gly,His,Ile,Lys,Leu,Met,Asn,Pro,Gln,Arg,Ser,
      Thr,Val,Trp,Tyr

<400> SEQUENCE: 6

Xaa Xaa Xaa Xaa Xaa Xaa Xaa Xaa Xaa Xaa Xaa Xaa Xaa Xaa Xaa Xaa
1               5                   10                  15

Xaa Lys Xaa Xaa Xaa Xaa Xaa Xaa Xaa Xaa Xaa Xaa Xaa Xaa Xaa
            20                  25                  30

Xaa Xaa Xaa Cys
        35

<210> SEQ ID NO 7
<211> LENGTH: 36
<212> TYPE: PRT
<213> ORGANISM: Artificial Sequence
<220> FEATURE:
<223> OTHER INFORMATION: synthesized polypeptide
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (2)..(18)
<223> OTHER INFORMATION: Xaa amino acids 2-18 plus 20-36 total no more
      than 18
<220> FEATURE:
<221> NAME/KEY: MISC_FEATURE
<222> LOCATION: (3)..(18)
<223> OTHER INFORMATION: Xaa one or more amino acids 3-18 may be present
      or absent: Xaa represents amino acid(s):
      Ala,Cys,Asp,Gln,Phe,Gly,His,Ile,Lys,Leu,Met,Asn,Pro,Gln,Arg,Ser,
      Thr,Val,Trp,Tyr
<220> FEATURE:
<221> NAME/KEY: MISC_FEATURE
<222> LOCATION: (3)..(18)
<223> OTHER INFORMATION: Xaa one or more amino acids 3-18 may be present
      or absent: Xaa represents amino acid(s):
```

```
        Ala,Cys,Asp,Gln,Phe,Gly,His,Ile,Lys,Leu,Met,Asn,Pro,Gln,Arg,Ser,
        Thr,Val,Trp,Tyr
<220> FEATURE:
<221> NAME/KEY: MISC_FEATURE
<222> LOCATION: (19)..(19)
<223> OTHER INFORMATION: Lys is labeled with fluorophore
<220> FEATURE:
<221> NAME/KEY: MISC_FEATURE
<222> LOCATION: (20)..(36)
<223> OTHER INFORMATION: Xaa amino acids 20-36 plus 2-18 total no more
        than 18
<220> FEATURE:
<221> NAME/KEY: MISC_FEATURE
<222> LOCATION: (20)..(20)
<223> OTHER INFORMATION: Xaa can be any naturally occurring amino acid
<220> FEATURE:
<221> NAME/KEY: MISC_FEATURE
<222> LOCATION: (21)..(36)
<223> OTHER INFORMATION: Xaa one or more of amino acids 21-36 may be
        present or absent Xaa represents amino acid(s):
        Ala,Cys,Asp,Gln,Phe,Gly,His,Ile,Lys,Leu,Met,Asn,Pro,Gln,Arg,Ser,
        Thr,Val,Trp,Tyr

<400> SEQUENCE: 7

Cys Xaa Xaa Xaa Xaa Xaa Xaa Xaa Xaa Xaa Xaa Xaa Xaa Xaa Xaa Xaa
1               5                   10                  15

Xaa Xaa Lys Xaa Xaa Xaa Xaa Xaa Xaa Xaa Xaa Xaa Xaa Xaa Xaa
            20                  25                  30

Xaa Xaa Xaa Xaa
        35

<210> SEQ ID NO 8
<211> LENGTH: 10
<212> TYPE: PRT
<213> ORGANISM: Artificial Sequence
<220> FEATURE:
<223> OTHER INFORMATION: SYNTHESIZED POLYPEPTIDE
<220> FEATURE:
<221> NAME/KEY: MISC_FEATURE
<222> LOCATION: (10)..(10)
<223> OTHER INFORMATION: Lys is labeled with Fluorophore

<400> SEQUENCE: 8

Cys Trp Thr Gly Ser Pro His Asp Thr Lys
1               5                   10
```

SENSITIVE METHOD TO ANALYSE FREE PEG-MALEIMIDE

FIELD OF THE INVENTION

The present invention relates generally to a novel method using HPLC and fluorescence detection of free PEG-mal in PEGylated proteins and PEG-mal raw materials by adding a fluorescent label to the free PEG-mal.

BACKGROUND OF THE INVENTION

Polyethylene glycol (PEG) is a versatile polymer with hydrophylic and hydrophobic properties that is widely used to conjugate with therapeutic proteins and peptides. The resultant derivatives are compounds that exhibit increased circulatory half-life, reduced immunogenicity and antigenicity, and increased resistance to proteolysis. The covalent attachment of PEG to proteins is known as PEGylation and it requires chemical modification or activation of the hydroxyl terminal group of the polymer. Several chemical groups have been used; in recent years, PEG modified with maleimide (PEG-mal) have gained popularity in the development of therapeutic proteins. PEG-mal reacts more efficiently and specifically with thiol groups in the protein or peptide of interest. Although the excess of PEG-mal is removed during purification, small amount may still be present in the final drug substance and must be considered as a product related impurity. Therefore, a method with high specificity and sensitive is desirable to evaluate not only the residual PEG-mal present in the purified PEGylated protein but also to evaluate raw materials. Since PEG-mal does not possess chemical structural features that allows its specific and sensitive detection in solution, peptide probes that contain both, a free thiol group and a fluorescent tag have been designed. This approach coupling with High Performance Liquid Chromatography (HPLC) separation significantly improve the specificity and sensitivity for free PEG-mal detection and quantitation.

SUMMARY OF THE INVENTION

The present invention provides a method to detect free PEG-mal in a solution comprising adding a fluorescent peptide probe to said solution; separating the peptide probe solution on a HPLC column and detecting the fluorescent tag attached to the free PEG-mal.

Certain criterions are considered in the design of the peptide probe. First, the peptide must contain an amino acid to provide the thiol group to react with PEG-mal. Second, it must contain a second amino acid to allow the attachment of the desired fluorescence label. Third, the peptide probe must be soluble in aqueous solution.

The peptide probe of the invention comprises the amino acid sequence of SEQ ID NO: 1, SEQ ID NO: 2, SEQ ID NO:3, SEQ ID NO:4, SEQ ID NO:5, SEQ ID NO: 6 and SEQ ID NO: 7.

The peptide probe of the invention further comprises a length of from 2 to 20 amino acids, alternatively from 2 to 10 amino acids in length, preferably 2 amino acids in length.

The peptide probe of the invention further comprises a fluorescent tag selected from the group of fluorophore consisting of fluorescein, biotin, derivatives of rhodamine (TRITC), coumarin and cyanine.

The peptide probe of the invention may comprise blocked N-terminus and/or the C-terminus.

The method of the invention adds the fluorescent peptide probe to the sample solution in a molar ratio of from 1:3 to 1:12 PEG-maleimide to fluorescent peptide probe, alternatively the fluorescent peptide probe is added at a molar ratio of from 1:3 to 1:10 PEG-maleimide to fluorescent peptide probe, more preferably the fluorescent peptide probe is added at a molar ratio of 1:6 PEG-maleimide to fluorescent peptide probe.

The method of the invention may be utilized to detect free PEG-mal in PEGylated protein solution. Alternatively, the method of the invention may be utilized to determine the percent active-PEG present in raw material.

BRIEF DESCRIPTION OF THE DRAWINGS

FIG. 1 shows the fluorescent peptide probes utilized in Example 1.

FIG. 5 shows the chromatograms of fluorescent peptide probe (A), PEG-maleimide P40 KB, un-derivatized (B), and PEG-maleimide P40 KB derivatized with the fluorescent peptide probe (C). Detection at 433 nm (excitation)/519 nm (emission).

DETAILED DESCRIPTION OF THE INVENTION

Figure 2A:
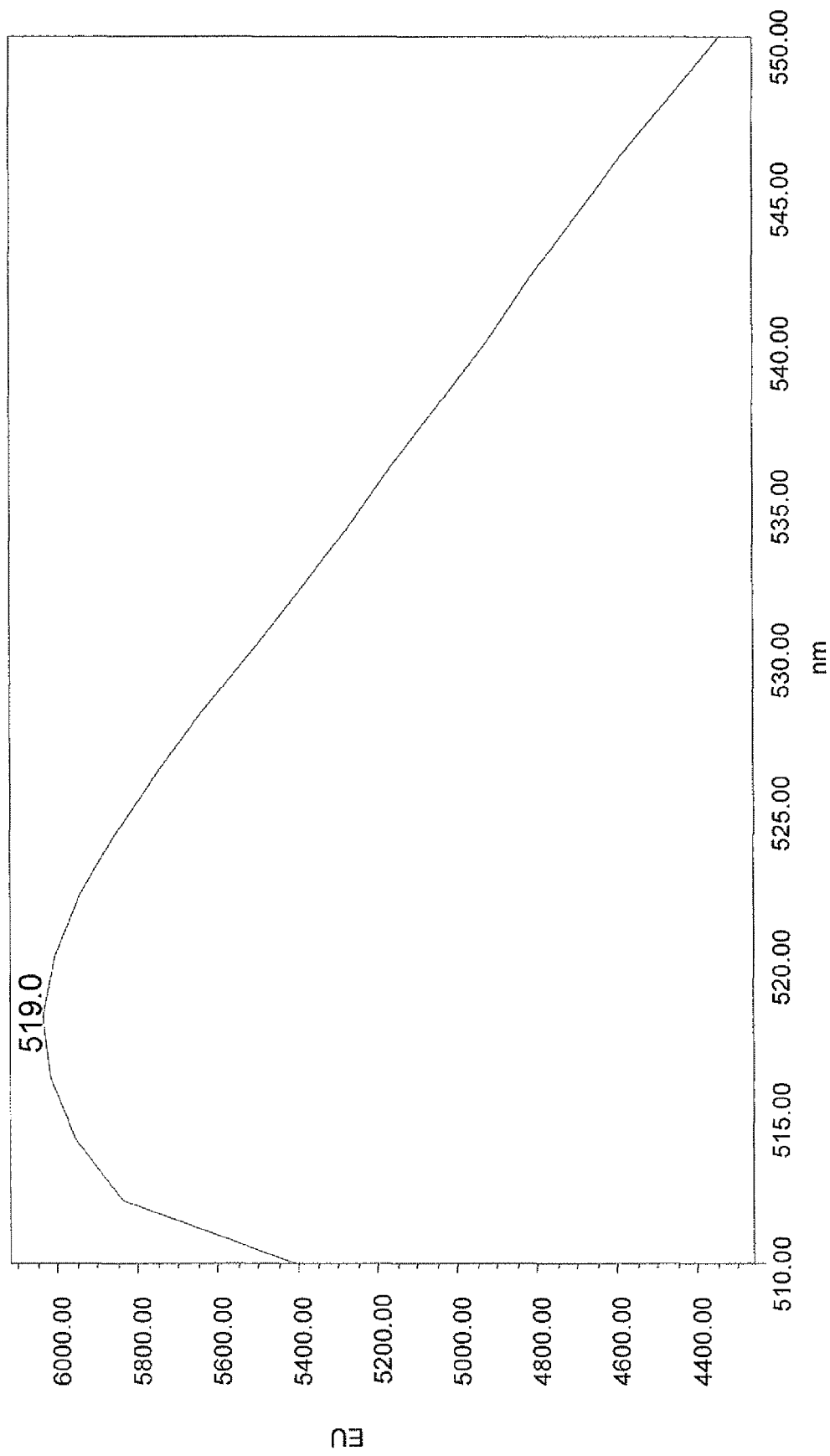
FIGS. 2A and 2B show the emission and excitation scan of 10AA fluorescent peptide probe.

As utilized herein:

"PEGylated protein" is a protein, or a fragment thereof, having a polyethylene glycol (PEG) moiety covalently bound to an amino acid residue of the protein.

"Polyethylene glycol" or "PEG" is a polyalkylene glycol compound or a derivative thereof, with or without coupling agents or derivatization with coupling or activating moieties (e.g., with thiol, triflate, tresylate, azirdine, oxirane, or preferably with a maleimide moiety). "PEG-mal" is polyethylene glycol linked to a maleimide moiety.

Description of the peptide probe of the invention is facilitated by listing the relationship between the one-letter symbols and the three-letter abbreviations for amino acids as follows:

| One-Letter Symbol | | Three-Letter Abbreviation |
|---|---|---|
| A | alanine | ala |
| C | cysteine | cys |
| D | aspartic acid | asp |
| E | glutamic acid | gln |
| F | phenylalanine | phe |
| G | glycine | gly |
| H | histidine | his |
| I | isoleucine | ile |
| K | lysine | lys |
| L | leucine | leu |
| M | methionine | met |
| N | asparagine | asn |
| P | proline | pro |
| Q | glutamine | gln |
| R | arginine | arg |
| S | serine | ser |
| T | threonine | thr |
| V | valine | val |
| W | tryptophan | trp |
| Y | tyrosine | tyr |

Naturally occurring amino acids can be generally classified as being polar or non-polar as follows:

```
Polar:      S, T, C, Y, D, N, E, Q, R, H, K
Non-polar:  G, A, V, L, I, M, F, W, P.
```

Amino acid residues can be subclassified into four major subclasses as follows:

Acidic: The residue has a negative charge due to loss of H ion at physiological pH and the residue is attracted by aqueous solution so as to seek the surface positions in the conformation of a peptide, in which it is contained, when the peptide is in aqueous medium at physiological pH.

Basic: The residue has a positive charge due to association with H ion at physiological pH and the residue is attracted by aqueous solution so as to seek the surface positions in the conformation of a peptide, in which it is contained, when the peptide is in aqueous medium at physiological pH.

Neutral/non-polar: The residues are not charged at physiological pH and the residue is repelled by aqueous solution so as to seek the inner positions in the conformation of a peptide, in which it is contained, when the peptide is in aqueous medium. These residues are also designated "hydrophobic" herein.

Neutral/polar: The residues are not charged at physiological pH, but the residue is attracted by aqueous solution so as to seek the outer positions in the conformation of a peptide, in which it is contained, when the peptide is in aqueous medium.

It is understood, of course, that in a statistical collection of individual residue molecules some molecules will be charged, and some not, and there will be an attraction for or repulsion from an aqueous medium to a greater or lesser extent. To fit the definition of "charged", a significant percentage (at least approximately 25%) of the individual molecules are charged at physiological pH. The degree of attraction or repulsion required for classification as polar or non-polar is arbitrary, and, therefore, amino acids specifically contemplated by the invention have been specifically classified as one or the other. Amino acids not specifically named above can be classified on the basis of known behavior.

Amino acid residues can be further subclassified as cyclic or noncyclic, and aromatic or nonaromatic (which are self-explanatory classifications with respect to the side chain substituent groups of the residues), and as small or large. The residue is considered small if it contains a total of 4 carbon atoms or less, inclusive of the carboxyl carbon. Small residues are always nonaromatic.

For the naturally occurring protein amino acids, subclassification according to the foregoing scheme is as follows:

Acidic: Aspartic acid and Glutamic acid;
Basic/noncyclic: Arginine, Lysine;
Basic/cyclic: Histidine;
Neutral/polar/small: Threonine, Serine and Cysteine;
Neutral/polar/large/nonaromatic: Threonine, Asparagine, Glutamine;
Neutral/polar/large/aromatic: Tyrosine;
Neutral/non-polar/small: Alanine;
Neutral/non-polar/large/nonaromatic: Valine, Isoleucine, Leucine, Methionine;
Neutral/non-polar/large/aromatic: Phenylalanine and Tryptophan.

The amino acid proline, although technically within the group neutral/non-polar/large/cyclic and nonaromatic, is a special case due to its known effects on the secondary conformation of peptide chains, and is not, therefore, included in this defined group, but is included as a group of its own.

The nomenclature used to describe compounds of the present invention follows the conventional practice wherein the amino group is assumed to be to the left and the carboxyl group to the right of each amino acid in the peptide. In the formulas representing selected specific embodiments of the present invention, the amino- and carboxyl-terminal groups, although often not specifically shown, will be understood to be in the form they would assume at physiological pH values, unless otherwise specified. Thus, the N-terminal $NH^+_3$ and C-terminal $OH^-$ at physiological pH are understood to be present though not necessarily specified and shown, either in specific examples or in generic formulas.

A "fluorophore" is a component of the peptide probe which provides the fluorescent marker for the method of the invention. It will absorb energy of a specific wavelength and re-emit energy at a different (but equally specific) wavelength. The amount and wavelength of the emitted energy depend on both the fluorophore and the chemical environment of the fluorophore.

An object of the present invention is to provide a sensitive method of detecting free PEG-mal in PEGylated proteins and accurately quantitate the activity of PEG-mal raw materials by utilizing a labeled peptide probe that adds a fluorescent label to the free PEG-mal which is easily separated by HPLC.

Certain criterions are required in the design of the peptide probe of the invention. First, the peptide probe must contain an amino acid, such as cysteine, to provide a thiol group to react with PEG-mal. Second, it must contain a second amino acid with a free amine group, such as lysine, to enable the attachment of the desired fluorescence label. Third, the peptide probe must be soluble in aqueous solution.

An example of the peptide probe of the invention comprises at least a cysteine (C) and a fluorescent labeled lysine [$K_{FL}$] as exemplified below, wherein (N) is an amino acid and x is 0 to 18, alternatively x is 0 to 13, preferably x is 0 to 8. The cysteine may be positioned at the N-terminus or C-terminus.

| | |
|---|---|
| C(N)$_x$[K$_{FL}$] | (SEQ ID NO: 1) |
| [K$_{FL}$](N)$_x$C | (SEQ ID NO: 2) |

Alternatively the peptide probe of the invention described above may have the N-terminus and/or C-terminus blocked, as exemplified below, wherein "Ac-" is a blocked N terminus and "-amide" is a blocked C terminus.

| | |
|---|---|
| Ac—C(N)$_x$[K$_{FL}$] | (SEQ ID NO: 3) |
| C(N)$_x$[K$_{FL}$]-amide | (SEQ ID NO: 4) |
| Ac—C(N)$_x$[K$_{FL}$]-amide | (SEQ ID NO: 5) |

Alternatively the labeled lysine of the invention described above may be positioned at the N-terminus or C-terminus or internally, as exemplified below, wherein the y is from 1 to 17, alternatively y is 1 to 12, preferably y is 1 to 7, wherein y totals no greater than 18, 13 or 8 amino acids, respectively.

| | |
|---|---|
| (N)$_y$[K$_{FL}$](N)$_y$C | (SEQ ID NO: 6) |
| C(N)$_y$[K$_{FL}$](N)$_y$ | (SEQ ID NO: 7) |

One knowledgeable in the art would know that the selection of the (N) amino acids should take into consideration the hydrophobicity of each amino acid as the peptide must be soluble in aqueous solution.

One knowledgeable in the art would know that the peptide probes described above may be ordered from suppliers, such as Sigma, that are capable of manufacturing the peptides or may be self manufactured by methods known in the art. Methods of manufacture are described in Pennington, M. W. et al., *Peptide Synthesis Protocols*, Humana Press Inc. (1994) and Benoiton, N. L., *Chemistry of Peptide Synthesis*, CRC Press (2006), both references incorporated herein by reference.

The peptide probe may be added to a solution containing free PEG-mal where the thiol group (HS-C) of the cysteine reacts with PEG-mal thereby attaching the fluorescent label [K$_{FL}$] to the free PEG-mal.

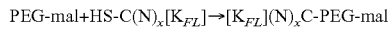

PEG-mal+HS-C(N)$_x$[K$_{FL}$]→[K$_{FL}$](N)$_x$C-PEG-mal

The reaction is carried out using excess amount of the fluorescent peptide probe at a molar ratio of from 1:3 to 1:12 (PEG-maleimide to fluorescent peptide probe), alternatively from 1:3 to 1:10, preferably 1:6 (PEG-maleimide to fluorescent peptide probe).

As shown in Example 1, two fluorescent peptide probes were designed to demonstrate the versatility of this approach, one with ten amino acids (AA) and the other with two amino acids, both containing fluorescein as a fluorophore (FIG. 1). Although fluorescein was used in Example 1, any other fluorophore (a molecule in an excited state which is capable of exhibiting fluorescence) that can be chemically attached to the peptide described above can be used. Examples of fluorophore include, but are not limited to, fluorescein, biotin, derivatives of rhodamine (TRITC), coumarin and cyanine.

The labeled free PEG-mal may be separated through HPLC and identified by the fluorescent tag. High-performance liquid chromatography (HPLC) is a form of liquid chromatography to separate compounds that are dissolved in solution. Generally, HPLC instruments consist of a reservoir of mobile phase, a pump, an injector, a separation column, and a detector. Compounds are separated by injecting the sample mixture onto the column. The different components in the mixture pass through the column at different rates due to differences in their partitioning behavior between the mobile liquid phase and the stationary phase. HPLC is a popular method of analysis because it is easy to learn and use and is not limited by the volatility or stability of the sample compound. The different types of HPLC include: Aqueous normal phase chromatography, partition chromatography, normal phase chromatography, displacement chromatography, reverse phase chromatography, size exclusion chromatography, ion exchange chromatography, bioaffinity chromatography and isocratic flow and gradient elution.

The peptide probe of the invention may be used to detect free PEG-mal in any solution comprising PEGylated protein as described above or to quantitate PEG-mal raw material.

Figure 11:
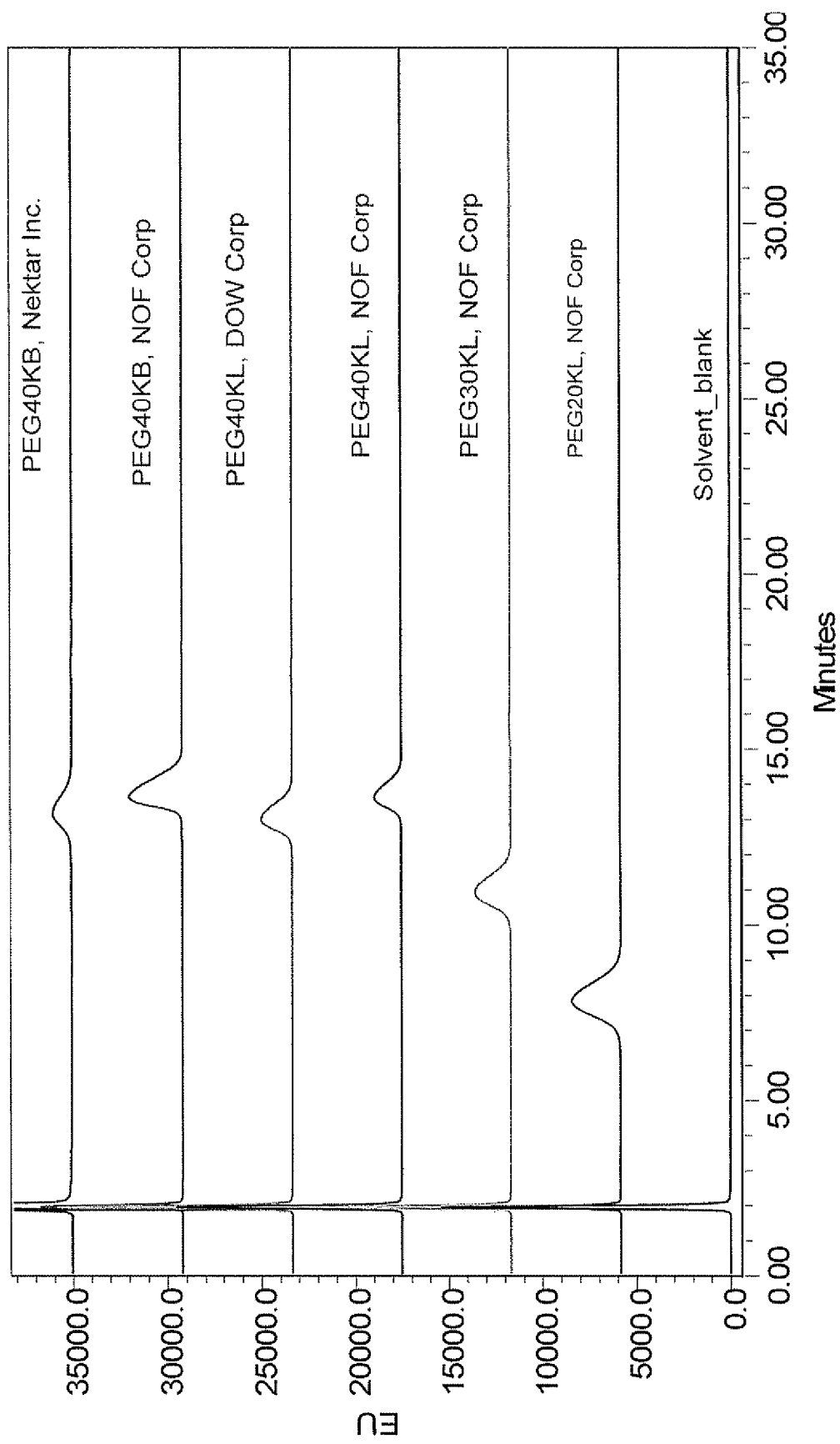
FIG. 11 shows RP-HPLC/fluorescence chromatograms of PEG-maleimide raw material derivatized with the fluorescent peptide probe of the invention.
Figure 12:
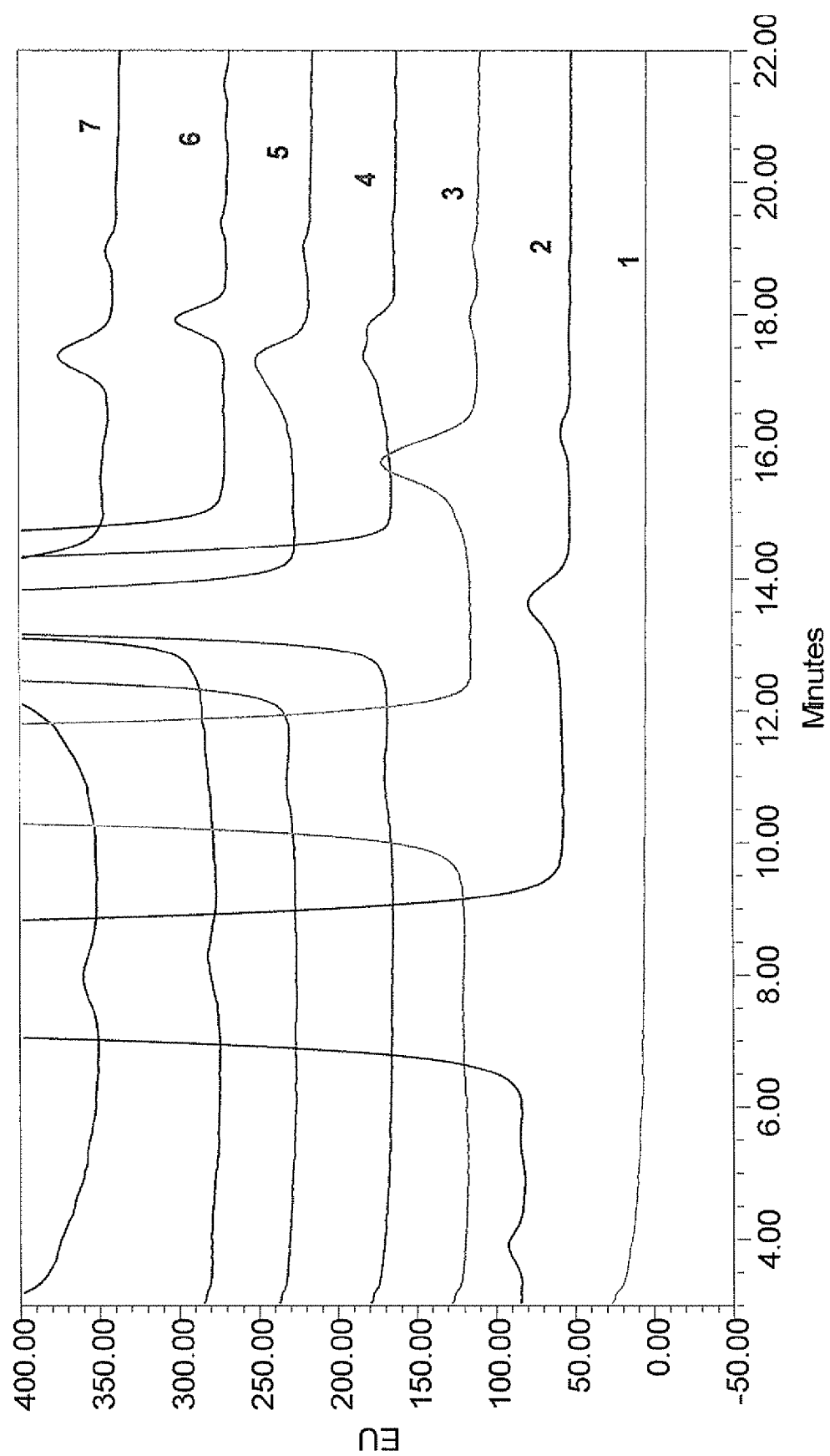
FIG. 12 shows RP-HPLC/fluorescence expanded chromatograms showing PEG-maleimide related impurities. 1=blank (buffer+fluorescent peptide probe), 2=PEG20KL, 3=PEG30KL, 4=PEG40KL, 5=PEG40KL (DOW Corp), 6=PEG40 KB, 7=PEG40 KB (Nektar).

As shown in FIGS. 11 and 12, the fluorescent peptide probe may also be utilized to determine the percent of active PEG-mal present in the raw material and highlight impurities in the PEG-mal raw material.

The invention will be more fully understood by reference to the following examples. They should not, however, be construed as limiting the scope of the invention. All citations throughout the disclosure are hereby expressly incorporated by reference.

Example 1 This Example describes the HPLC method development, the performance assessment for the method linearity, specificity, precision, accuracy, limit of detection (LOD) and limit of quantitation (LOD LOQ), and application of the method to the analysis of PEGylated protein samples.

Materials

PEG-maleimide of different molecular weights and purified research PEGylated protein samples were used for this study as indicated in Table 1.

TABLE 1

PEG-mal and Purified PEGylated Protein Samples

| Name | Description |
|---|---|
| PEG-mal 20KL | MW ~20K, linear, product NOF ME200MA |
| PEG-mal 20KBi-functional | MW ~20K, linear bi-functional, product NOF DE200MA |
| PEG-mal 30KL | MW ~30K, linear, product NOF ME300MA |
| PEG-mal 40KL | MW ~40K, linear, product DOW 008-013 |
| PEG-mal 40KB | MW ~40K, branch, product NOF GL2 400MA |
| Sample 1 | PEGylated protein (PEG-mal 40KB) sample, 1.8 mg/mL |
| Sample 2 | PEGylated protein (PEG-mal 40KB) sample, 2.2 mg/mL |
| Sample 3 | PEGylated protein (PEG-mal 40KB) sample, 2.5 mg/mL |
| Sample 4 | PEGylated protein (PEG-mal 40KL) sample, 1.8 mg/mL |
| Sample 5 | PEGylated protein (PEG-mal 40KL) sample, 5.2 mg/mL |
| Sample 6 | PEGylated protein(PEG-mal 40KL) sample, 6.2 mg/mL |

Method

High Performance Liquid Chromatography was performed using a polymer column, PLRP-S 150 mm×4.6 mm, 300 Å, 5 μm (Varian Inc.) at 60° C. on a Waters 2695 system equipped with a PDA-UV detector and a fluorescence detector. Mobile phase A consisted of water 0.1% trifluoroacetic acid (TFA), and mobile phase B consisted of 90% acetonitrile (ACN)/0.1% TFA. Samples were eluted from the column at a flow rate of 1.0 mL/min with the following linear gradient:

Gradient Condition:

| Time (min) | % A | % B |
|---|---|---|
| 0.0 | 50 | 50 |
| 24.0 | 40 | 60 |
| 28.0 | 15 | 85 |
| 28.1 | 50 | 50 |
| 35.0 | 50 | 50 |

Figure 2B:
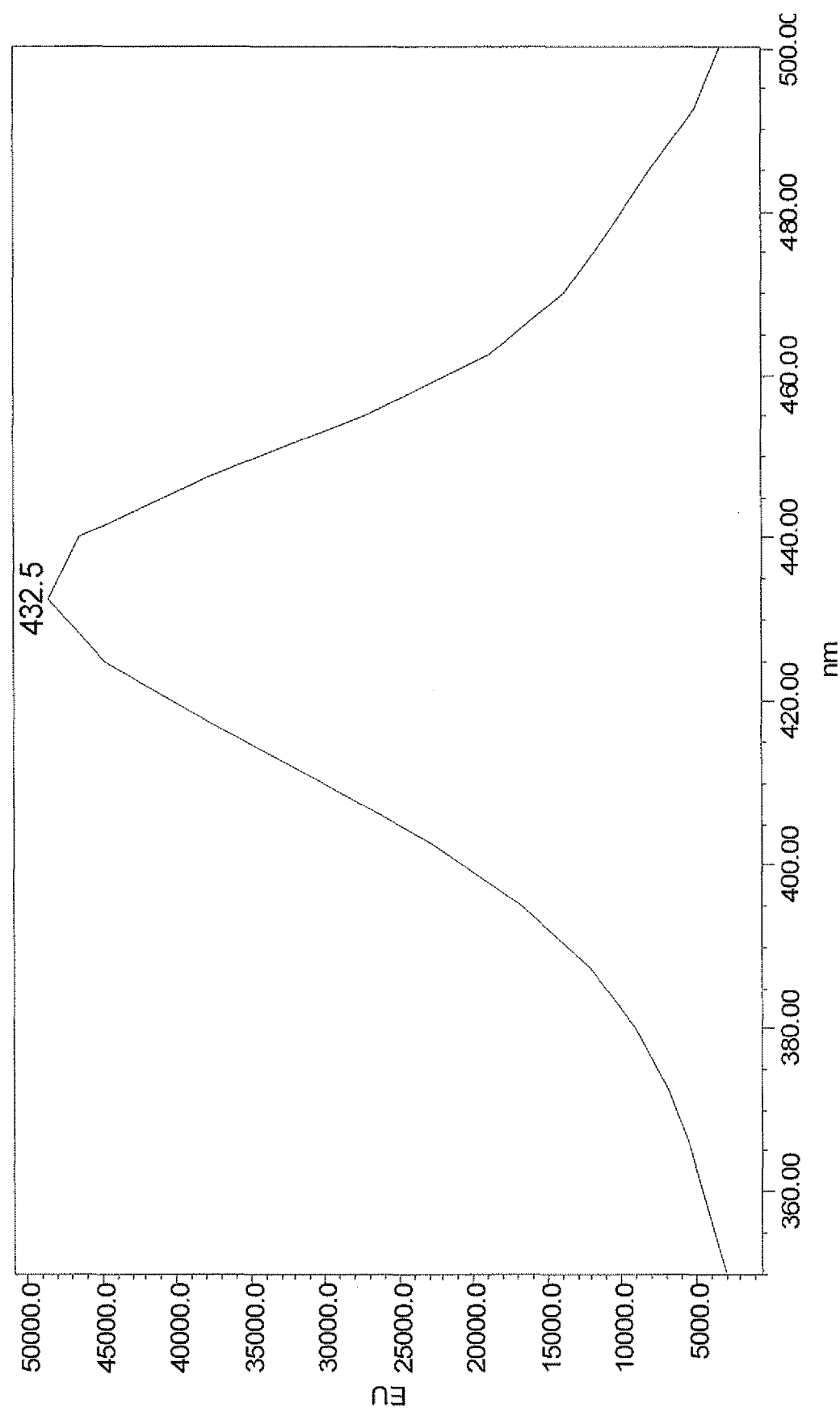

Fluorescence detection was monitored at 433 nm (excitation) and 519 nm (emission) as determined by the emission and excitation fluorescence scan of the fluorescence peptide probe, FIG. 2. The complete chromatographic sample profile was monitor at 278 nm (excitation) and 350 nm (emission) and by UV detection at 214 nm.

Sample Preparation

Figure 3:
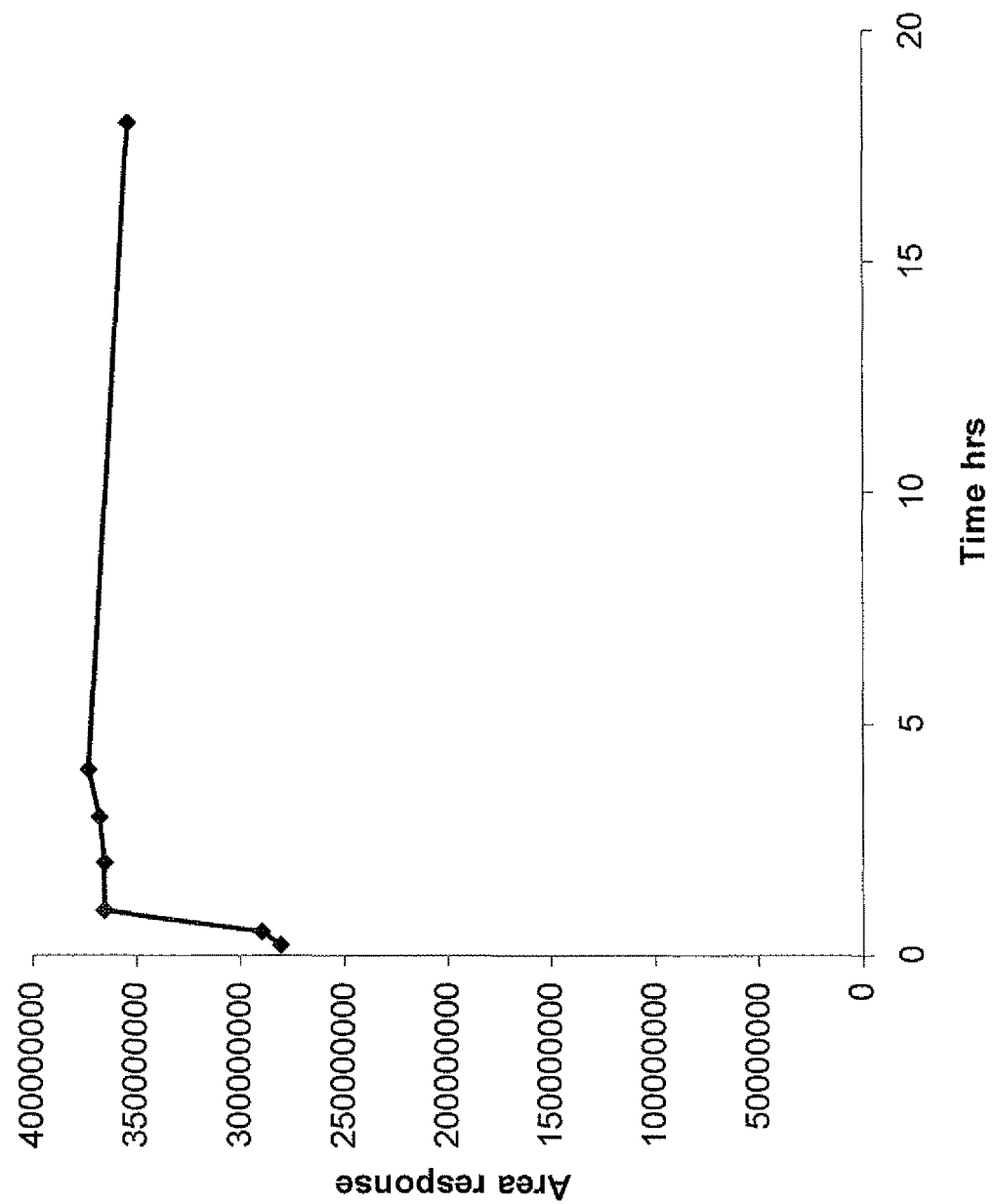
FIG. 3 shows the time course reaction for PEG-mal derivative.

PEG-mal was diluted in 10 mM phosphate buffer pH 7.2 to 1 mg/mL. Fluorescence peptide probe at a concentration of 1 mg/mL was prepared in the same buffer. This solution was centrifuged before added to the PEG-mal or to the PEGylated protein sample, 10 µL of the probe to 100 µL of sample. The reaction is carried out using excess amount of the fluorescent peptide probe at a molar ratio of 1:6 (PEG-maleimide to fluorescent peptide probe). Other molar ration, 1:3 and 1:12, were also used successfully in determining the amount of PEG-maleimide up to 1 mg/mL in sample solution, although the linear range reported in this study cover up to 0.750 mg/mL. Reaction time of about 1 hour under dark was generally enough as shown in FIG. 3. Sample volume of 25 µL was injected into the HPLC system.

Chromatographic Profile of PEG-mal

Figure 4A:
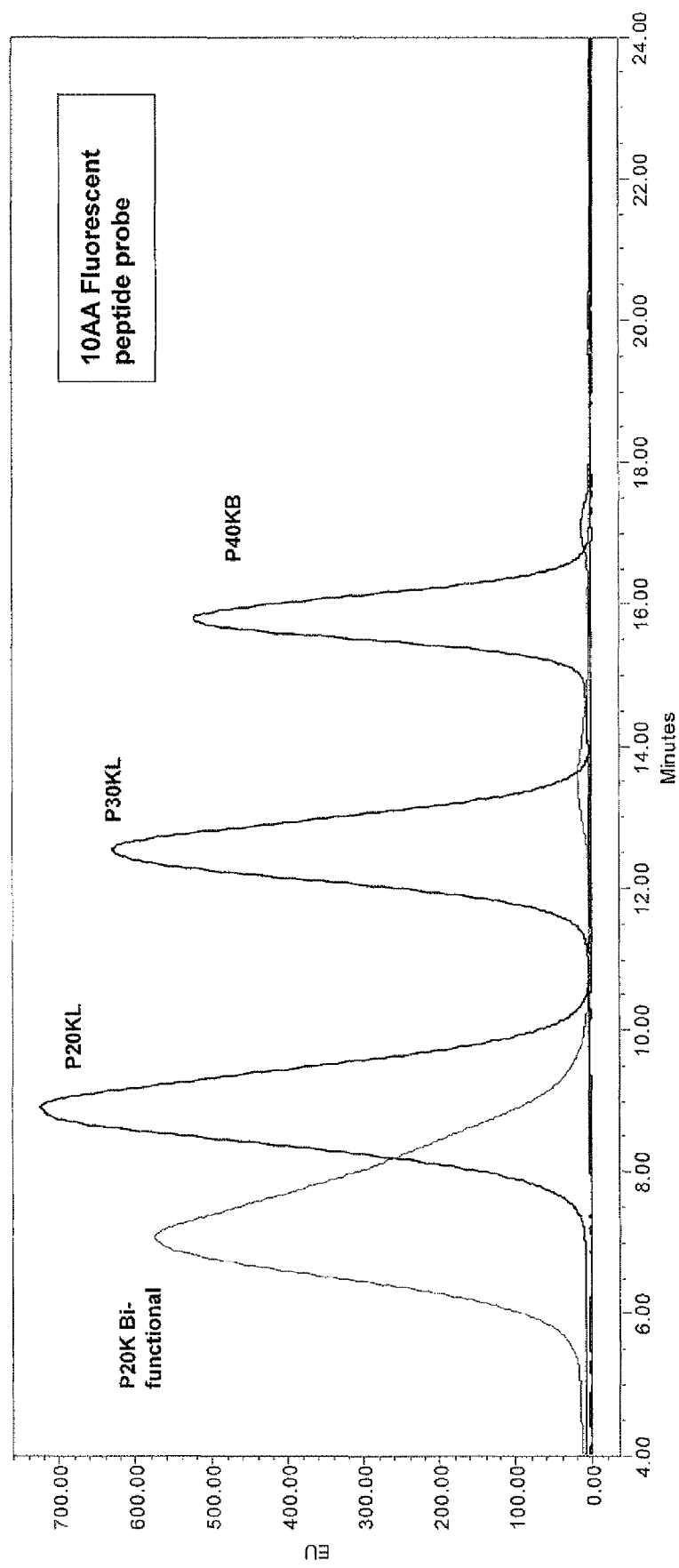
FIGS. 4A and 4B show the chromatographic profiles for several PEG-mal derivatives.
Figure 4B:
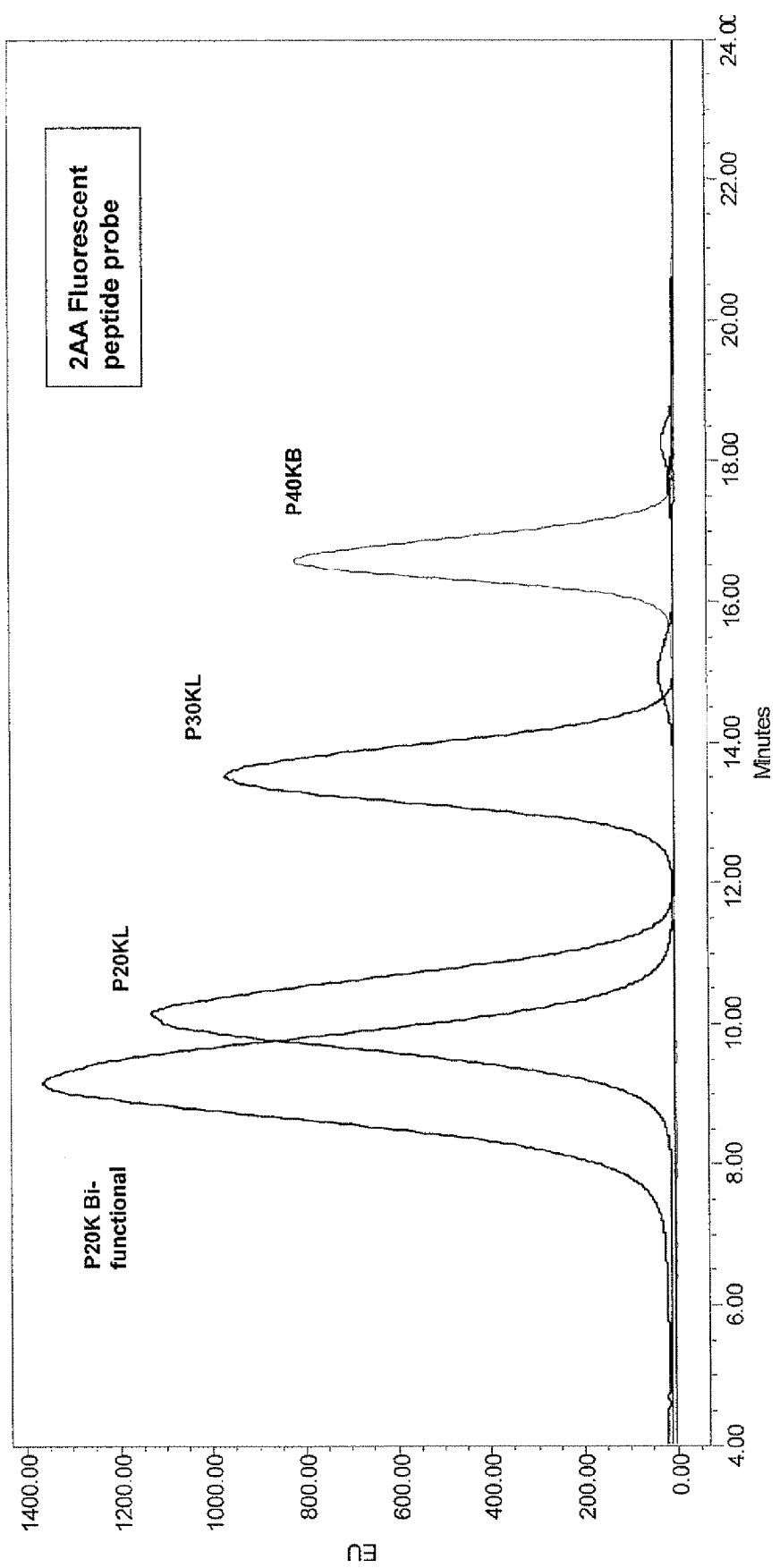

FIG. 4 shows the chromatographic profile of several PEG-mal after derivatization with both fluorescence peptide probes. The PEG-mal elution order is from lower MW to higher MW. Other later eluting minor peaks are observed for PEG-mal 20K Bi-functional and PEG-mal 30KL. These minor peaks are also PEG-mal derivatives of higher MW present in the sample.

Specificity

The specificity of the method was assessed by a complete chromatographic separation of PEG-mal derivative. In addition, it was shown that the sample matrix does not interfere with the PEG-mal derivative as shown in FIG. 5.

Linearity

Figure 9:
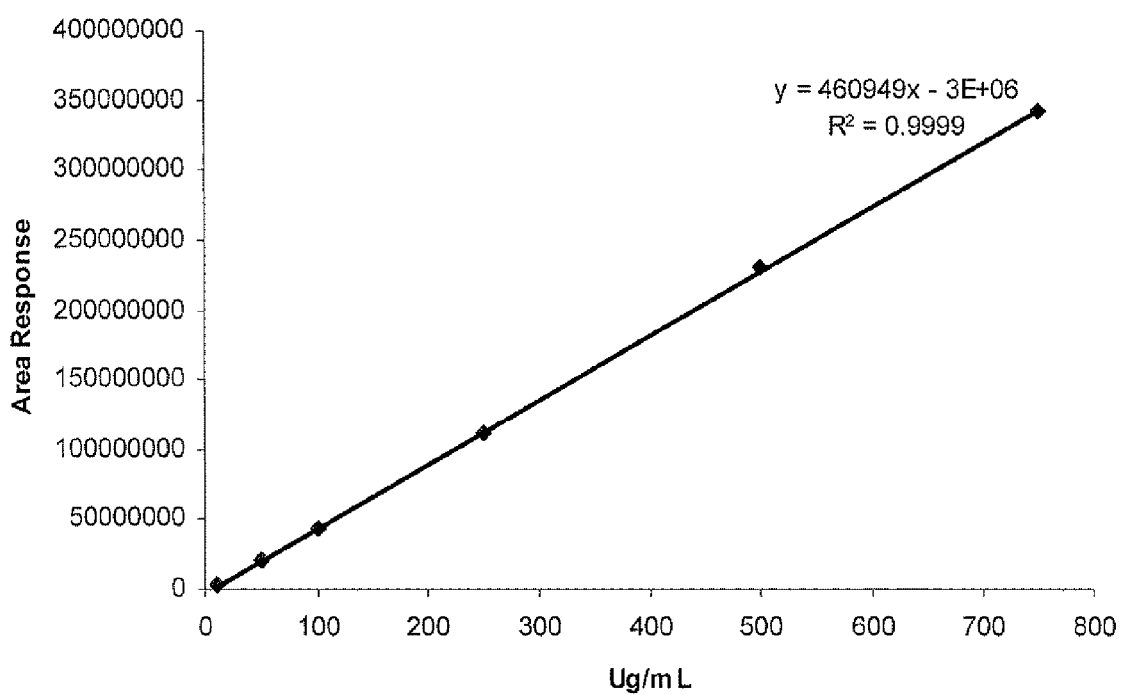
FIG. 9 shows the linear regression plot of the peak areas obtained for PEG-mal derivative (MW~40K branch) against the concentration of the test solution.

The linearity of the method was investigated and proven to be linear in the range 10 µg/mL-750 µg/mL. The results for the evaluation of linearity are given in Table 2. The linear regression plot of the peak areas obtained for PEG-mal derivative (MW~40K branch) against the concentration of the test solution are shown in FIG. 9.

TABLE 2

Results for the evaluation of the linearity

| Concentration (µg/mL) | Response | Calculated Value | % Deviation |
|---|---|---|---|
| 10.0 | 2818848 | 11.64 | −14.11 |
| 50.0 | 20236075 | 49.43 | 1.16 |
| 100.0 | 43100987 | 99.03 | 0.98 |
| 250.0 | 111379727 | 247.16 | 1.15 |
| 500.0 | 230203444 | 504.94 | −0.98 |
| 750.0 | 342149812 | 747.80 | 0.29 |

Precision

The assessment of the precision of the method as well as the stability of the PEG-mal derivative was proven by three samples injections over three consecutive days. The results are summarized in Table 3. The relative standard deviations below 3% for both fluorescent peptide probes confirm an acceptable level of precision.

TABLE 3

Summary of Results for the Evaluation of Precision

| Fluorescent Peptide probe of 10AA | | Fluorescent Peptide probe of 2AA | |
|---|---|---|---|
| Day | Response | Day | Response |
| 1 | 111379728 | 1 | 171910964 |
| 2 | 107178438 | 2 | 171415941 |
| 3 | 108782364 | 3 | 163455248 |
| Mean | 109113510 | Mean | 168927384 |
| STDV | 2120130.34 | STDV | 4745468.26 |
| % RSD | 1.94 | % RSD | 2.81 |

Accuracy

Figure 6:
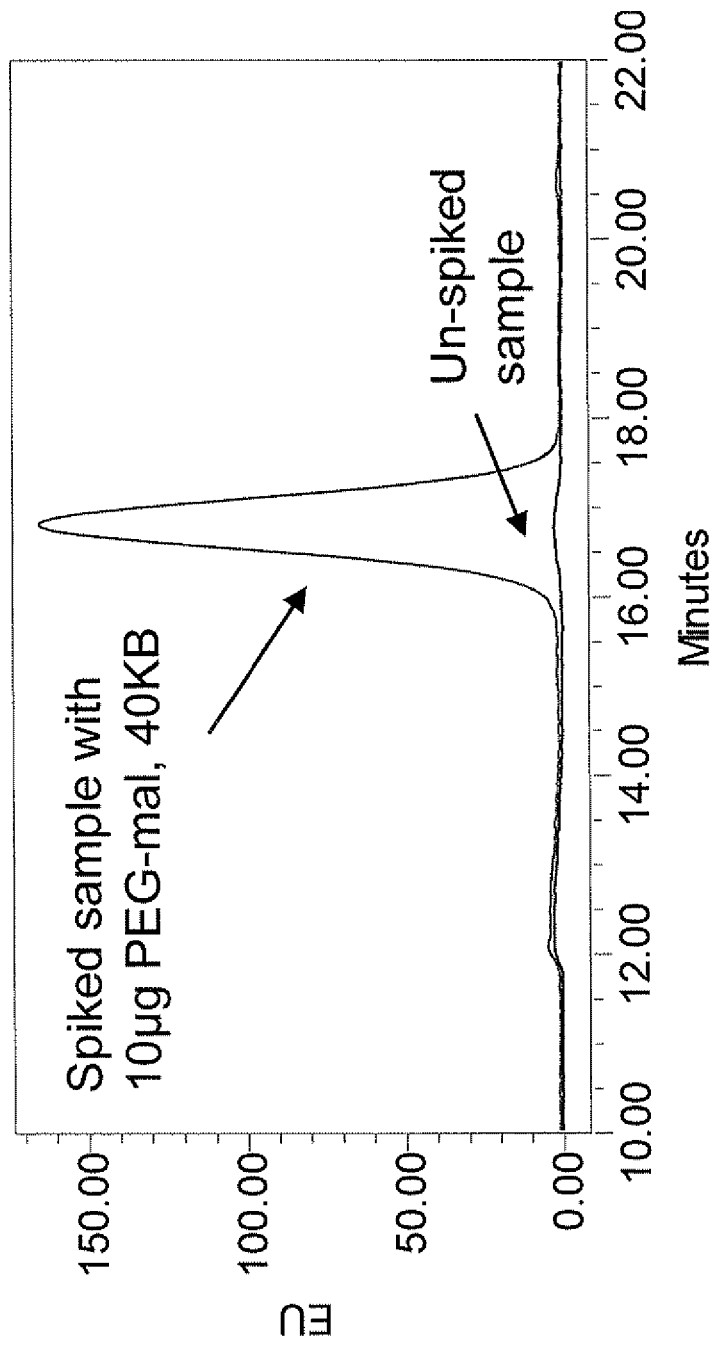
FIG. 6 shows the chromatograms of spiked and un-spiked PEGylated antiCD28 research sample for the evaluation of accuracy. PEGylated protein sample spiked with 10 µg of PEG-maleimide, P40 KB. The amount of 10.03 µg was found yielding a percent recovery of 100.3%.

For the evaluation of the accuracy a PEGylated protein sample was spiked with an accurate amount of PEG-mal (MW~40K, branch) and the percent recovery was calculated (FIG. 6). A percent recovery of 100.3% was calculated.

Estimated LOD and LOQ

Figure 7:
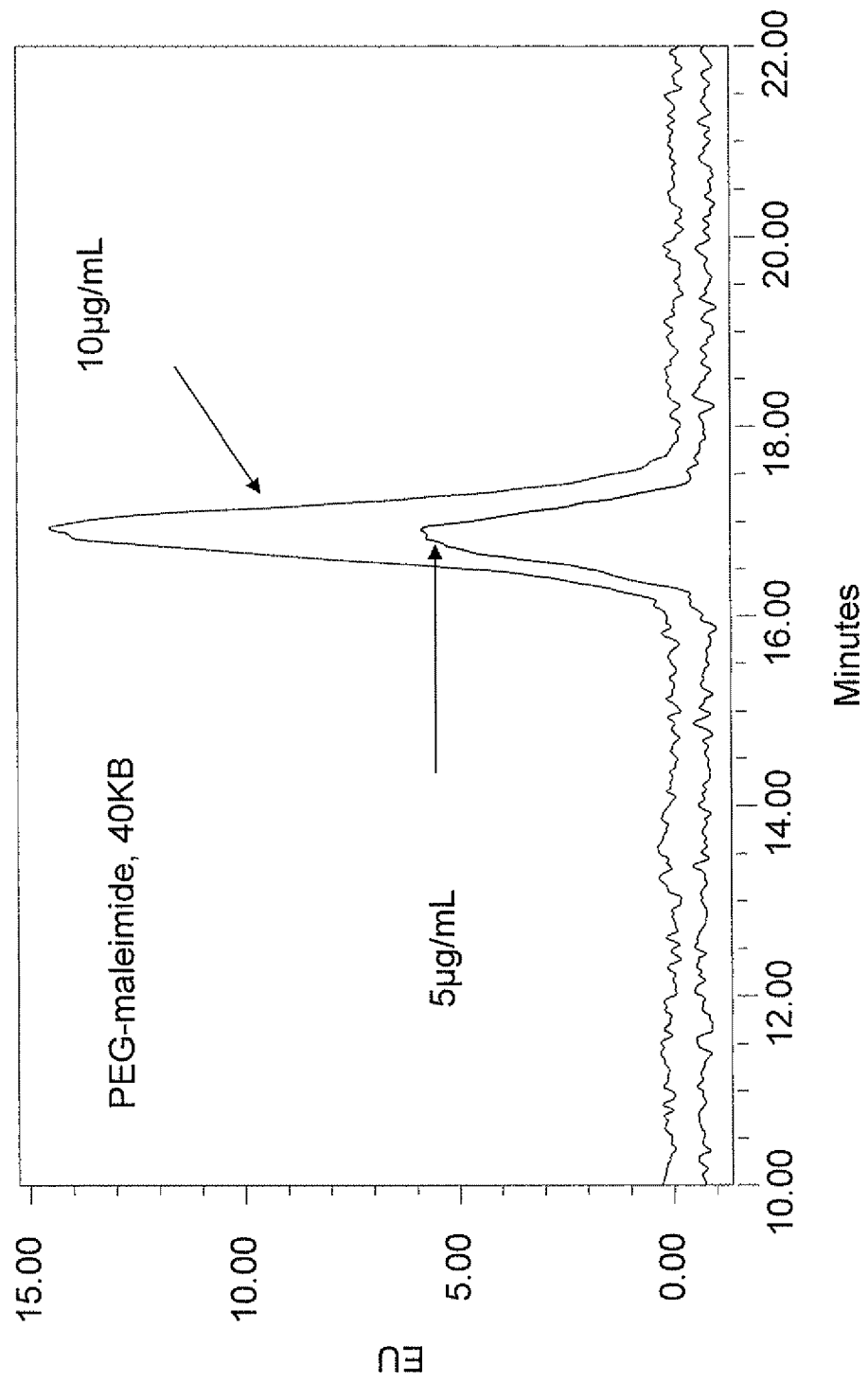
FIG. 7 shows the chromatograms of low level concentration of PEG-maleimide, 40 KB for evaluation of LOD and LOQ. LOD and LOQ estimated at 3 µg/mL and 10 µg/mL, respectively.
Figure 10:
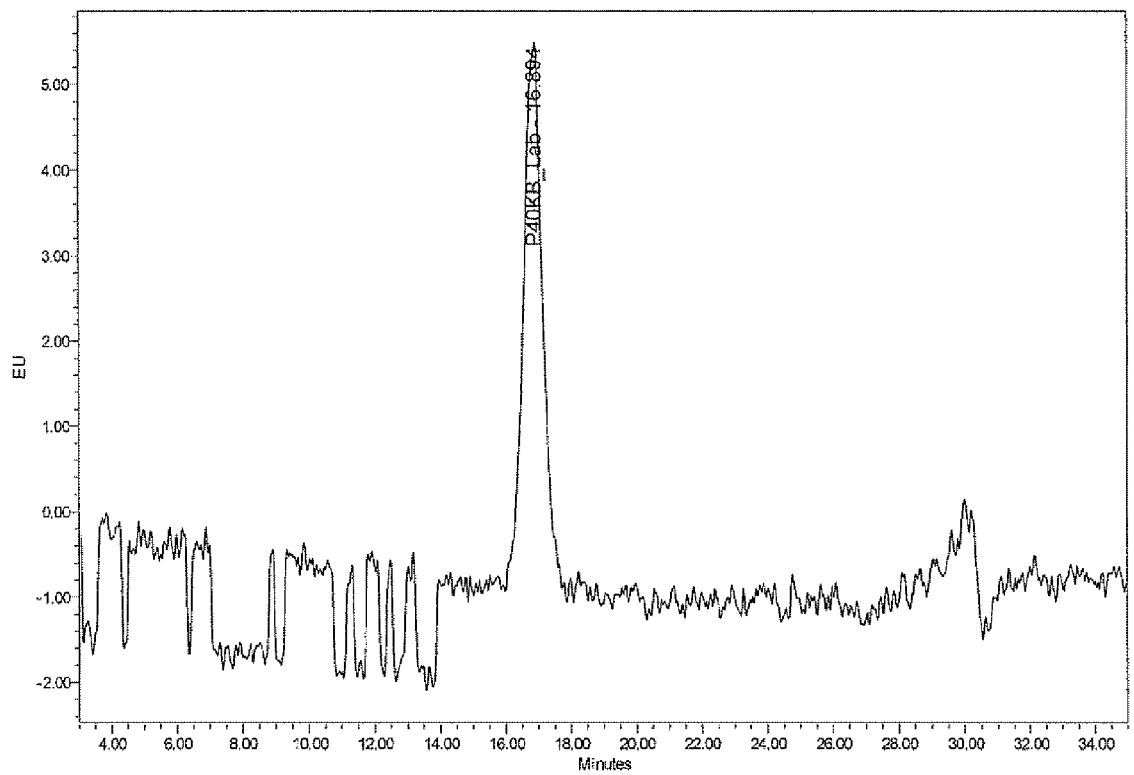
FIG. 10 shows a chromatogram of a 5 µg/mL PEG-mal 40 KB solution showing the instrument calculated signal to noise ratio (s/n).

The estimated LOD was based on 3 times the signal to noise ratio (s/n) of a low level concentration, 5 µg/mL, of PEG-mal 40 KB and the LOQ was estimated as 3.3 times the LOD (10 times s/n). LOD and LOQ were estimated to be about 3 µg/mL and 10 µg/mL, respectively. Chromatograms of PEG-mal derivative of 5 µg/mL and 10 µg/mL are shown in FIG. 7. A chromatogram of a 5 µg/mL PEG-mal 40 KB solution showing the instrument calculated signal to noise ratio (s/n) is shown in FIG. 10.

Analysis of PEGylated Protein Samples

Figure 8:
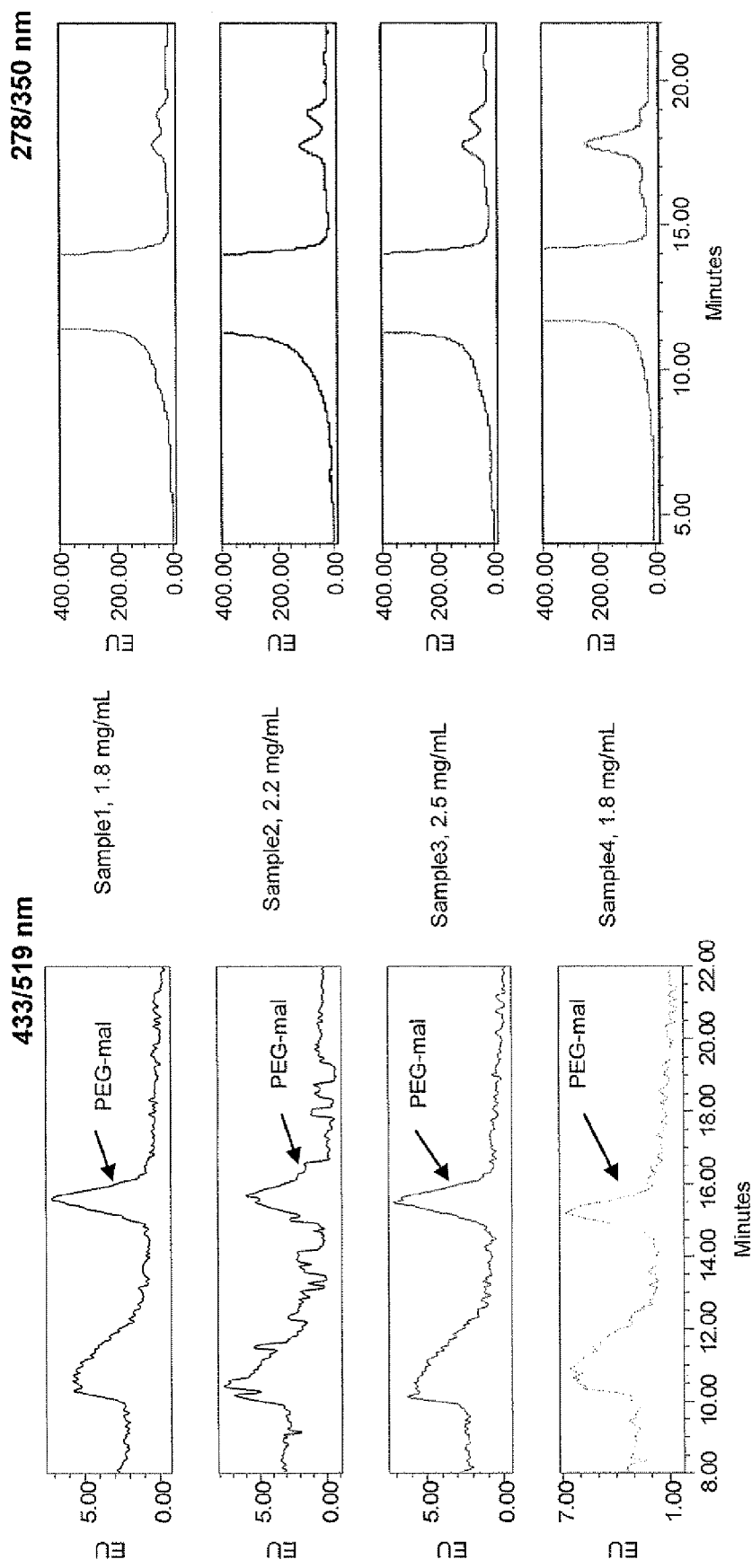
FIG. 8 shows the chromatograms of analyzed purified antiCD28 research samples PEGylated with PEG-maleimide 40 KB. Quantitation level estimated at LOD or non-detectable. Chromatograms on the right side (278 nm/350 nm) show the PEGylated protein and other PEGylated protein related peaks.
Figure 8:
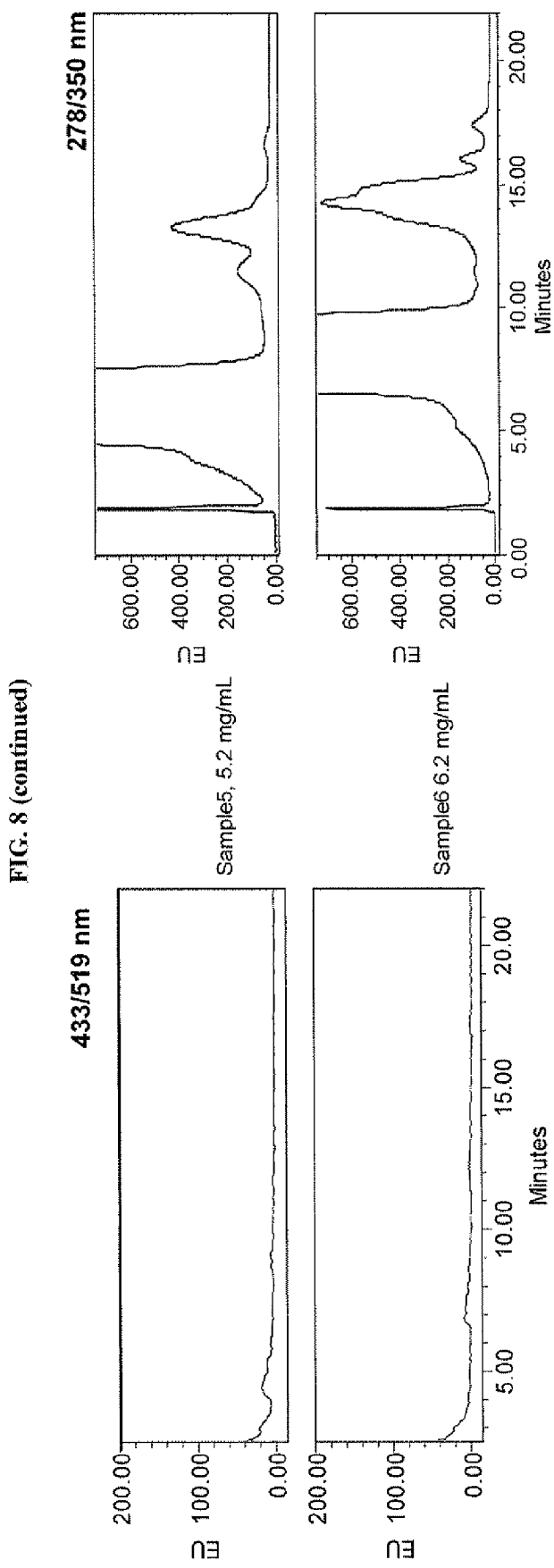

Several PEGylated protein samples were analyzed by the method. The results for all samples were estimated to be at LOD level. FIG. 8 shows the chromatograms of the PEGylated protein samples analyzed.

CONCLUSION

A novel HPLC method for the analysis of polyethylene glycol-maleimide (PEG-mal) or active-PEG using fluorescence detection has been developed. The assessment of the method parameters such as specificity, linearity, precision, accuracy, estimated LOD and LOQ confirm the suitability of the procedure for the analysis of free PEG-mal in PEGylated proteins and PEG-mal raw materials. In addition, the method can provide information about other PEG-mal or active-PEG related impurities as well as the percent of active-PEG present in the raw material. The method is specific to the analysis of active-PEG, any non-active PEG (PEG without maleimide group) will not be detected. It is linear in the range of 10 µg/mL to 750 µg/mL. The method precision, expressed as % RSD, is less than 3.0%. The accuracy expressed as % recovery is 100.3%. The estimated LOD and LOQ are 3 and 10 µg/mL, respectively.

What is claimed:

1. A method to detect free polyethylene glycol-maleimide (PEG-mal) in a solution comprising free PEG-mal and PEGylated protein said method comprising the steps of
   (a) adding the fluorescent labeled peptide probe consisting of SEQ ID NO: 1, to said solution;
   (b) allowing the fluorescent labeled peptide probe in the solution of step (a) to react under dark conditions with the free PEG-mal present in the solution to provide fluorescent labeled PEG-mal;
   (c) separating by fractionation the fluorescent labeled PEG-mal from the PEGylated protein using high performance liquid chromatography (HPLC) wherein the fluorescent fraction identifies the free PEG-mal.

2. The method of claim 1 wherein the fluorophore is selected from the group consisting of fluorescein, derivatives of rhodamine (TRITC), coumarin and cyanine.

3. The method of claim 1 wherein the fluorescent labeled peptide probe is added at a molar ratio of from 1:3 to 1:12 PEG-maleimide to peptide probe.

4. The method of claim 3 wherein the fluorescent labeled peptide probe is added at a molar ratio of from 1:3 to 1:10 PEG-maleimide to peptide probe.

5. The method of claim 4 wherein the fluorescent labeled peptide probe is added at a molar ratio of 1:6 PEG-maleimide to peptide probe.

6. A method to detect free polyethylene glycol-maleimide (PEG-mal) in a solution comprising free PEG-mal and PEGylated protein said method comprising the steps of
   (a) adding a fluorescent labeled peptide probe to said solution;
   (b) allowing the fluorescent labeled peptide probe in the solution of step (a) to react under dark conditions with the free PEG-mal present in the solution to provide fluorescent labeled PEG-mal; (c) separating by fractionation the fluorescent labeled PEG-mal from the PEGylated protein using high performance liquid chromatography (HPLC) wherein the fluorescent fraction idetifies the free PEG-mal; and
   wherein the fluorescent labeled peptide probe comprises a fluorophore attached to a peptide sequence consisting of 2 to 20 amino acids wherein at least one amino acid in the peptide sequence is a cysteine at the N-terminus or C-terminus of the peptide sequence wherein the thiol group of the cysteine remains free to react with the PEG-mal in the solution; wherein at least one amino acid of the remainder of the peptide sequence comprises a free amine group to which the fluorophore is attached and wherein the fluorescent labeled peptide probe is soluble in aqueous solution.

7. The method of claim 6 wherein the fluorophore is selected from the group consisting of fluorescein, derivatives of rhodamine (TRITC), coumarin and cyanine.

8. The method of claim 6 wherein the fluorescent labeled peptide probe is added at a molar ratio of from 1:3 to 1:12 PEG-maleimide to peptide probe.

9. The method of claim 8 wherein the fluorescent labeled peptide probe is added at a molar ratio of from 1:3 to 1:10 PEG-maleimide to peptide probe.

10. The method of claim 9 wherein the fluorescent labeled peptide probe is added at a molar ratio of 1:6 PEG-maleimide to peptide probe.

* * * * *